(12) United States Patent
Skerl et al.

(10) Patent No.: US 10,363,170 B2
(45) Date of Patent: Jul. 30, 2019

(54) APPARATUS FOR CORNEAL CROSSLINKING

(71) Applicant: WAVELIGHT GMBH, Erlangen (DE)

(72) Inventors: Katrin Skerl, Bad Doberan (DE); Armin Wellhöfer, Schwaig (DE); Christof Donitzky, Eckental (DE)

(73) Assignee: Novartis AG (CH)

( * ) Notice: Subject to any disclaimer, the term of this patent is extended or adjusted under 35 U.S.C. 154(b) by 0 days.

(21) Appl. No.: 14/384,082

(22) PCT Filed: Jan. 28, 2013

(86) PCT No.: PCT/EP2013/051574
§ 371 (c)(1),
(2) Date: Sep. 9, 2014

(87) PCT Pub. No.: WO2014/114359
PCT Pub. Date: Jul. 31, 2014

(65) Prior Publication Data
US 2015/0313756 A1    Nov. 5, 2015

(51) Int. Cl.
*A61F 9/008* (2006.01)
*A61F 9/009* (2006.01)

(52) U.S. Cl.
CPC .............. *A61F 9/008* (2013.01); *A61F 9/009* (2013.01); *A61F 2009/00842* (2013.01); *A61F 2009/00872* (2013.01); *A61F 2009/00893* (2013.01)

(58) Field of Classification Search
CPC .......... A61F 9/001; A61F 9/007; A61F 9/008; A61F 9/009; A61F 2009/00842; A61F 2009/00872; A61F 2009/00893; A61M 37/00; A61B 18/20; A61B 6/08

USPC .............................. 606/3, 4; 604/20; 600/431
See application file for complete search history.

(56) References Cited

U.S. PATENT DOCUMENTS

| | | | |
|---|---|---|---|
| 5,549,632 A * | 8/1996 | Lai | A61F 9/00825 606/10 |
| 5,909,270 A * | 6/1999 | Moser | A61B 3/107 351/212 |
| 6,572,606 B2 * | 6/2003 | Kliewer | A61F 9/00806 606/10 |
| 2007/0123845 A1 | 5/2007 | Lubatschowski | |
| 2007/0230520 A1 * | 10/2007 | Mordaunt | A61F 9/008 372/23 |
| 2008/0208177 A1 * | 8/2008 | Mrochen | A61F 9/008 606/5 |

(Continued)

FOREIGN PATENT DOCUMENTS

| | | | |
|---|---|---|---|
| EP | 2407132 A1 * | 1/2012 | ......... A61F 9/00827 |
| JP | 2010-000382 A | 7/2010 | |

(Continued)

OTHER PUBLICATIONS

Juhasz et al., Corneal Refractive Surgery with Femtosecond Lasers, Jul./Aug. 1999, IEEE Journal of Selected Topics in Quantum Electronics, vol. 5, No. 4, pp. 902-910.*

*Primary Examiner* — Boniface N Nganga
(74) *Attorney, Agent, or Firm* — Keiko Ichiye, Esq.

(57) ABSTRACT

An apparatus for corneal crosslinking, the use of the apparatus for corneal crosslinking, and a method for corneal crosslinking are provided. The apparatus comprises a source of laser radiation; a scanner device for scanning the laser radiation; and a control computer for controlling the scanner device.

8 Claims, 3 Drawing Sheets

(56) References Cited

U.S. PATENT DOCUMENTS

| | | | | |
|---|---|---|---|---|
| 2010/0103676 A1* | 4/2010 | Noeth | ............... | G02B 5/02 |
| | | | | 362/276 |
| 2010/0210996 A1* | 8/2010 | Peyman | ............... | A61F 7/007 |
| | | | | 604/20 |
| 2011/0282333 A1* | 11/2011 | Herekar | ............... | A61F 9/00821 |
| | | | | 606/5 |
| 2012/0215155 A1* | 8/2012 | Muller | ............... | A61F 9/0079 |
| | | | | 604/20 |

FOREIGN PATENT DOCUMENTS

| | | | | |
|---|---|---|---|---|
| WO | 2004075681 A2 | 9/2004 | | |
| WO | WO 2007084694 A2 * | 7/2007 | ............. | A61F 9/008 |
| WO | 2012145159 A1 | 10/2012 | | |

* cited by examiner

APPARATUS FOR CORNEAL CROSSLINKING

CROSS REFERENCE TO RELATED APPLICATIONS

This application is a section 371 national stage phase of International Application No. PCT/EP2013/051574, filed 28 Jan. 2013, titled "APPARATUS FOR CORNEAL CROSS-LINKING," which is hereby incorporated by reference in its entirety.

TECHNICAL FIELD

The present disclosure generally relates to refractive surgery, for example, LASIK, and related ophthalmological procedures. More particularly, embodiments of the present disclosure relate to an apparatus for corneal crosslinking, the use of the apparatus, and a method for corneal crosslinking.

BACKGROUND

In ophthalmology, the technique of using a photosensitizer and electromagnetic radiation to change the biomechanical and biochemical properties of tissue, e.g., the cornea, for therapeutic purposes has been known for more than 10 years.

The human eyeball is bounded by the corneosclera. Due to internal eye pressure, the corneosclera, which contains collagen, has an approximately spherical shape. In the posterior eyeball region, the corneosclera consists of white sclera. The cornea, which is translucent to visible light, is situated in the anterior region.

Deformations of the corneosclera can cause ametropia. For example, axial myopia, a type of myopia, can result from a cornea and/or sclera longitudinal expansion of the eyeball. An ellipsoidal shaped corneal surface can cause a form of astigmatism or other high order aberration, which is called "irregular corneal curvature". Another defect of the cornea can be caused by progressive and irregular changes in corneal shape. This is typically known as ectasia. These ectatic changes are typically marked by corneal thinning and an increase in the anterior and/or posterior curvatures of the cornea, and often lead to high levels of myopia and astigmatism. The most common form of ectasia is keratoconus. In keratoconus, a pathological softening of the cornea leads to a progressive thinning and cone-shaped deformation of the cornea. As the bulging increases, the cornea becomes typically thinner below the center. It can fracture and become scarred, which can permanently reduce visual acuity. In these conditions, the corneal stroma is structurally weakened and biomechanically unstable.

Corneal crosslinking (which is also often referred to as cross-linking, corneal collagen crosslinking or corneal collagen cross-linking) is a technique which uses ultraviolet (UV) light or light in the blue spectrum and a photosensitizer to strengthen chemical bonds in the cornea and to thereby increase the corneal stiffness. The stiffening effect results from UV radiation of the photosensitizer. By means of the UV radiation, the photosensitizer is activated to cause corneal crosslinking. Corneal crosslinking involves the cross-linking of collagen fibres. UV light is used to bring about the crosslinking in the cornea, which results in the cornea becoming stronger and more rigid. The UV light that the cornea absorbs during the treatment causes crosslinking. The crosslinking will take place over a few days after the irradiation with the UV light.

In short, corneal cross-linking may be regarded as the process of placing a photosensitizer on or into the cornea followed by exposure to UV light, in order to stiffen the cornea.

In known techniques, the corneal epithelium is at least partially removed to introduce riboflavin as one example of a photosensitizer into the cornea, because the epithelium hinders the riboflavin from penetrating the cornea by acting as a barrier to the diffusion of the riboflavin molecules into the cornea. More recently, it has been proposed to create channels in the cornea by means of a laser device, to introduce riboflavin into the created channels and to irradiate the introduced riboflavin by means of a suitable additional UV light source. This requires that either the additional UV light source is moved to the patient or the patient is moved to the additional UV light source.

SUMMARY

There is a need to provide an improved technique for corneal crosslinking.

It has been found that light in the wavelength range from 190 nm to 500 nm, e.g., 270 nm, 366 nm or 445 nm, is appropriate for activating photosensitizer for corneal cross-linking, which are currently commonly used. However, other photosensitizers may be conceivable in the future, which may be activated by light in wavelength ranges differing from the aforementioned exemplary range.

In the present disclosure, an apparatus, a use of the apparatus, and a method are provided. Specific embodiments are described in the dependent claims.

According to a first aspect, an apparatus for corneal crosslinking is provided. The apparatus comprises: a source of laser radiation; a scanner device for scanning the laser radiation; and a control computer for controlling the scanner device. The control computer is programmed to control the scanner device to create in the cornea at least one incision for the introduction of or application of photosensitizer into or onto the cornea, and to activate the photosensitizer for corneal crosslinking.

The at least one incision may be or may comprise at least one cut and/or at least one channel incision. The at least one channel incision may be created for the introduction of photosensitizer into the cornea. For example, the at least one channel incision may form one or more channels for the introduction of photosensitizer. The at least one cut may be created for the application of photosensitizer onto the cornea.

In this way, the same source of laser radiation can be used for both creating the at least one incision, e.g., the at least one cut and/or the at least one channel incision, and activating the photosensitizer for corneal crosslinking.

The photosensitizer may comprise any suitable ingredients that stabilize corneal tissue, e.g., riboflavin (vitamin B2), lysyloxidase, transglutaminase, sugar aldehydes, ethylcarbodiimid, glutaraldehyde, formaldehyde or mixtures of these e.g. Karnovsky solution.

The control program may be executable on the control computer, the control program containing instructions that, when executed by the control computer, control the scanner device in the way set forth above. The scanner device for scanning the laser radiation may guide the laser radiation relative to the eye in order to create at least one incision, e.g., at least one cut and/or at least one channel incision. Further, optical components like optical mirrors and a focusing objective may be provided in the beam path of the laser radiation for focusing the laser radiation. The scanner device may be configured to transversely and longitudinally control the focal point of the laser radiation. In this context, "transverse" may refer to a direction at right angles to the direction of propagation of the laser radiation, and "longitudinal" may refer to the direction of beam propagation of the laser radiation.

Examples of sources of laser radiation include an attosecond laser, a femtosecond laser, a nanosecond laser, or a picosecond laser. By means of said sources, a LASIK procedure may be performed or lenticule incisions may be created. In such procedures, for example, a femtosecond laser cuts tissue of the eye by photodisruption of the tissue with the energy of the laser light, which creates laser inducted optical breakthrough (LIOB), which generate cavitation bubbles. In LASIK procedure, the laser system cuts a flap or cap in the stroma. The flap/cap is lifted or removed to ablate the exposed stroma using, e.g., an excimer laser in order to reshape the cornea. Pulsed lasers with pulse lengths in the picosecond, nanosecond, femtosecond and attosecond range are suitable for creating the at least one incision, e.g., the at least one cut and/or the at least one channel incision. The source of laser radiation provided in the apparatus according to the first aspect may be in a wavelength range of 300-1900 nanometers (nm), for example, a wavelength in the range of 300-650, 650-1050, 1050-1250, or 1100-1900 nm.

The control computer controlling the scanner device may be programmed to instruct the scanner device to move the foci of the laser radiation along a straight or curved line to yield LIOBs in the tissue in order to produce the at least one incision, e.g., the at least one cut and/or channel incision. The at least one incision may be created such that, on the one hand, the separation of the individual adjacent LIOB from each other (or "spacing" between the bubbles) may impair the structure and stability of the tissue as little as possible. On the other hand, in case at least one channel incision is created, the separation between the LIOBs forming the at least one channel incision may be so small that the photosensitizer, introduced into the at least one channel incision in the form of a solution penetrates into the tissue through the at least one channel incision in the desired manner, i.e., from LIOB to LIOB. In the regions between adjacent LIOBs, the photosensitizer therefore penetrates by diffusion.

It follows that in the sense of certain embodiments the term "channel" or "channel incision" is not necessarily to be thought of as a continuous cavity fully free of tissue, although on the other hand completely continuous channels or channel incisions can also be envisaged in certain embodiments. The term "channel" or "channel incision" as used herein in certain embodiments does not mean an incision area for creating a flap/cap as in LASIK. The term "cut" on the other hand, may be understood as a flap/cap, which may then be hardened by corneal crosslinking.

The at least one incision, e.g., the at least one channel incision, may at least partially be created by the laser radiation, wherein the LIOBs at least in part do not merge completely with one another. The distance between adjacent LIOBs may be in the range from 1 μm to 20 μm. For example, distance between adjacent LIOBs may be in the range from e.g., 1 μm to 10 μm; 3 μm to 5 μm; 7 to 10 μm; 10 to 15 μm; 15 to 20 μm.

In a first embodiment of the first aspect, it is possible to relocate the position of the eye to be treated relative to the apparatus. In this way, the laser radiation may be defocused, which may lead to a reduced fluence of the laser radiation in the cornea. It is conceivable to cause defocusing of the laser radiation in such a way that the fluence of the reduced laser radiation is below a threshold at which photodisruption occurs in the cornea. By relocating the position of the eye, the intensity of the laser radiation may be weakened which may lead to a reduced fluence of the laser radiation in the cornea. The mean power of the irradiation may be in the range of 3 to 100 mW/cm$^2$ or higher, for example, a range of 3-10; 10-30; 30-50; 50-80; 80-100 mW/cm$^2$.

In a second embodiment of the first aspect, the apparatus may comprise a fluence reduction component for reducing the fluence of the laser radiation. For example, the reduced fluence may be below a threshold at which corneal photodisruption occurs. The mean power of the irradiation may be in the range of 3 to 100 mW/cm$^2$ or higher, for example, a range of 3-10; 10-30; 30-50; 50-80; 80-100 mW/cm$^2$.

In consequence, the at least one channel incision may be created by dissecting the cornea by means of the laser radiation provided by the source for laser radiation. Then, photosensitizer may be introduced into the at least one channel incision. The laser radiation may then be modified by means of the fluence reduction component such that the fluence of the laser radiation may be reduced. The photosensitizer may then be activated by irradiating the photosensitizer with the laser radiation having the reduced fluence.

The fluence reduction component may be selectively introduced into the beam path of the laser radiation. It is conceivable that the fluence reduction component may be introduced into the beam path of the laser radiation in response to an instruction from the control computer. For example, the fluence reduction component may be configured to be moved into the beam path of the laser radiation. This movement may be any type of movement, e.g., a linear movement, a swinging movement or the like, by means of which the fluence reduction component can be moved from a first position, in which it is not introduced in the beam path of the laser radiation, to a second position, in which it is introduced in the beam path of the laser radiation, back to the first position and so on.

The fluence reduction component may be a, or may be part of a patient interface, a patient adapter or an applanation cone. The patient interface, patient adapter or applanation cone may interface with the cornea of the eye. In this case, by modifying at least one of the length of and the optical components within the patient interface, patient adapter or applanation cone, the fluence of the laser radiation can be suitably reduced.

In a first variant of the second embodiment, the fluence reduction component may comprise or may be configured as a widening component for widening of the beam of the laser radiation. By widening of the beam of the laser radiation, the laser radiation may be defocused, which may lead to a reduced fluence of the laser radiation in the cornea. It is conceivable to cause widening of the beam of the laser radiation in such a way that the fluence of the widened laser radiation is below a threshold at which photodisruption occurs in the cornea.

In a second variant of the second embodiment, the fluence reduction component may comprise or may be configured as a defocusing component for defocusing of the laser radiation. It is conceivable to cause defocusing of the laser radiation in such a way that the fluence of the defocused laser radiation is below a threshold at which photodisruption occurs in the cornea.

In a third variant of the second embodiment, the fluence reduction component may comprise or may be configured as a scattering component for scattering of the laser radiation. By scattering of the laser radiation, the fluence of the laser radiation in the cornea may be reduced. It is conceivable to cause scattering of the laser radiation in such a way that the fluence of the scattered laser radiation is below a threshold at which photodisruption occurs in the cornea.

In a fourth variant of the second embodiment, the fluence reduction component may comprise or may be configured as an energy reduction component for reducing the energy of the laser radiation as provided by the source. By means of the energy reduction component, the energy of the laser radiation as provided by the source of laser radiation may be reduced. The control computer may instruct the source of laser radiation to reduce the energy by an amount calculated by the control computer. It is conceivable to cause reduction of the energy in such a way that the fluence of the reduced laser radiation is below a threshold at which photodisruption occurs in the cornea.

According to a second aspect, the use of the apparatus for corneal crosslinking as described herein is provided.

According to a third aspect a method for corneal crosslinking is provided. The method comprises: providing laser radiation; scanning the laser radiation by means of a scanner device; and controlling the scanner device to create in the cornea at least one incision for the introduction of or application of photosensitizer into or onto the cornea, and to activate the photosensitizer for corneal crosslinking.

According to a variant of the method according to the third aspect, a method is taught combining the afore-mentioned method with a method of introducing a photosensitizer into the cornea of an eye. The variant of the method according to the third aspect may be combined with refractive surgery performed at the cornea, for example, refractive surgery in the form of LASIK. According to a further variant of the method according to the third aspect, a method is taught combining the method according to the third aspect with a method of applying a photosensitizer onto the cornea of an eye.

Embodiments of the present disclosure will now be described by way of example in greater detail with reference to the attached drawings, in which.

Referring now to the drawings, example embodiments of the disclosed apparatus and method are shown in detail. The following description is in no way intended to be exhaustive or to otherwise limit or restrict the accompanying claims to the specific embodiments shown in the drawings and disclosed herein. Although the drawings represent possible embodiments, the drawings are not necessarily to scale and certain features may be simplified, exaggerated, removed, or partially sectioned to better illustrate the embodiments. In addition, certain drawings may be in schematic form.

Although in the following, it is only referred to "a" channel incision or "the" channel incision, this is not intended to limit the number of channel incisions to a specific number. Rather, the term "channel" or "channel incision" as used below encompasses any suitable number of channels or channel incisions, e.g., one channel (incision) and two or more channels or channel incisions. Further, although in the following it is only referred to the creation of channel(s) or channel incision(s), other types of incisions like one or more cuts may also be created in a similar manner.

Figure 1:
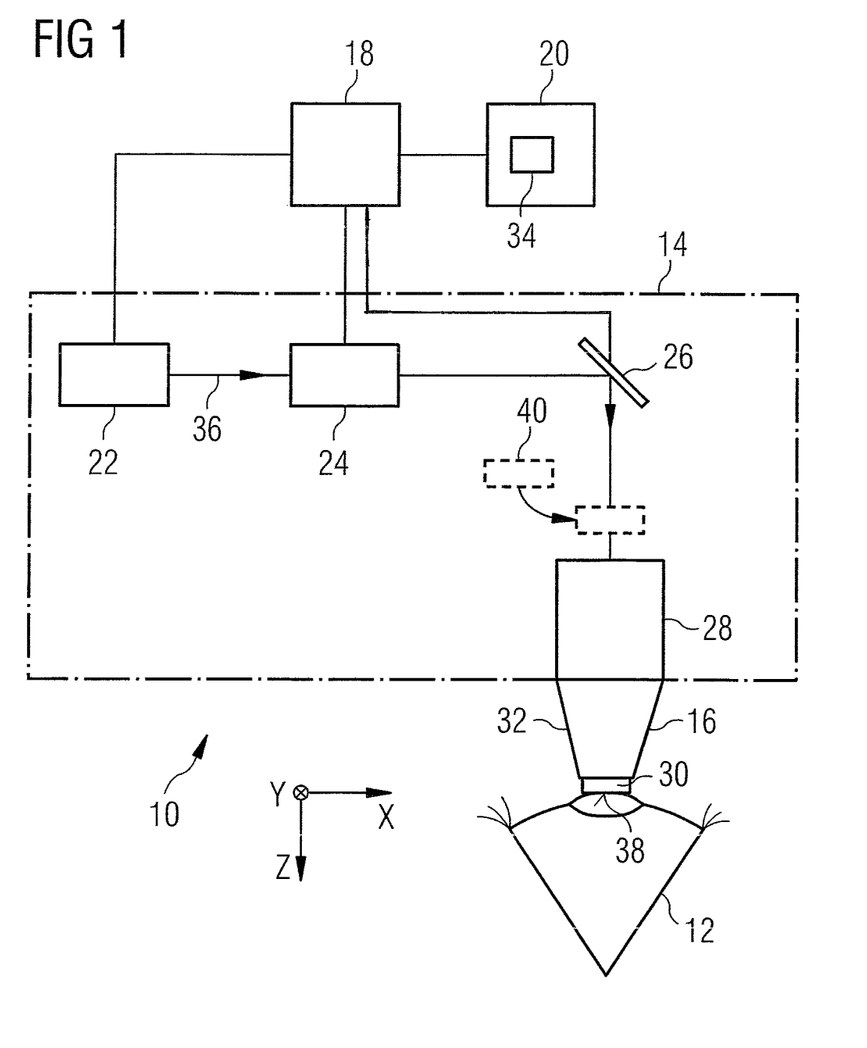
FIG. 1 schematically illustrates an example of an apparatus for corneal crosslinking in a human cornea according to an embodiment.

FIG. 1 illustrates an example embodiment of an apparatus 10 configured to create a channel in the cornea of an eye. In this embodiment, the apparatus 10 includes a laser device 14 and a control computer 18. The laser device 14 can create at least one channel incision in the cornea of a human eye using ultrashort-pulsed laser radiation. As used herein, ultrashort is intended to mean a pulse duration within the nanosecond, picosecond or femtosecond or attosecond range. The laser device 14 can create the channel incision as part of an eye-surgical treatment during which a photosensitizer is introduced into the created channel incision and the photosensitizer, which is used by way of example, is then irradiated with ultraviolet (UV) light or light in the blue spectrum in order to activate the photosensitizer for corneal crosslinking.

The laser device 14 may include controllable components that direct a focus of the pulsed laser radiation along a predetermined path within the cornea to create the channel incision.

In the illustrated example of FIG. 1, the apparatus 10 performs laser surgery on a human eye 12. The apparatus 10 includes the laser device 14, a patient adapter 16, the control computer 18, and a memory 20 may be coupled as exemplary shown. The memory 20 stores a control program 34. The laser device 14 includes a laser source 22, a scanner 24, one or more optical mirrors 26, and a focusing objective 28 may be coupled as exemplary shown. The patient adapter 16 includes a contact element 30 and a support sleeve 32 coupled as shown.

The laser source 22 generates a laser beam 36 with ultrashort pulses. The focal point of the laser beam 36 may create a laser-induced optical breakdown (LIOB) in tissues such as the cornea. The laser beam 36 may be precisely focused to allow for precise incisions in the corneal cell layers, which may reduce or avoid unnecessary destruction of other tissue.

The laser beam 36 may have any suitable wavelength, such as a wavelength in the range of 300-1900 nanometers (nm), for example, a wavelength in the range of 300-650, 650-1050, 1050-1250, or 1100-1900 nm. In the present example it is assumed without limitation that the laser beam 36 has a wavelength of 345 nm. The laser beam 36 may also have a relatively small focus volume, e.g., 5 micrometers ($\mu$m) or less in diameter. In certain embodiments, the laser source 22 and/or a delivery channel (not shown in the drawings) for the laser beam 36 may be in a vacuum or near vacuum.

The scanner 24, optical mirrors 26, and focusing objective 28 are in the beam path of the laser beam 36. The scanner 24 is configured to transversely and longitudinally control the focal point of the laser beam 36. "Transverse" refers to a direction at right angles to the direction of propagation of the laser beam 36, and "longitudinal" refers to the direction of beam propagation. The transverse plane may be designated as the x-y plane, and the longitudinal direction may be designated as the z-direction.

The scanner 24 may transversely direct the laser beam 36 in any suitable manner. For example, the scanner 24 may include a pair of galvanometrically actuated scanner mirrors that can be tilted about mutually perpendicular axes. As another example, the scanner 24 may include an electro-optical crystal that can electro-optically steer the laser beam 36. The scanner 24 may longitudinally direct the laser beam 36 in any suitable manner. For example, the scanner 24 may include a longitudinally adjustable lens, a lens of variable refractive power, or a deformable mirror that can control the z-position of the beam focus. The focus control components of the scanner 24 may be arranged in any suitable manner along the beam path, e.g., in the same or different modular units.

The one or more optical mirrors 26 direct the laser beam 36 towards the focusing objective 28. For example, an optical mirror 26 may be an immovable deviating mirror. As an alternative, an optical element that can refract and/or diffract the laser beam 36 may be provided in place of an optical mirror 26.

The focusing objective 28 focusses the laser beam 36 onto the eye 12 and more specifically onto a cornea of the eye 12. The focusing objective 28 may be separably coupled to the patient adapter 16. The focusing objective 28 may be any suitable optical device, such as an f-theta objective.

The patient adapter 16 interfaces with the cornea of the eye 12. The sleeve 32 couples to the focusing objective 28 and retains the contact element 30. The contact element 30 is transparent or translucent to the laser radiation and has an abutment face 38 that interfaces with the cornea and may level a portion of the cornea. In certain embodiments, the abutment face 38 is planar and forms a planar area on the cornea. The abutment face 38 may be on an x-y plane, so that the planar area is also on an x-y plane. In other embodiments, the abutment face need not be planar, e.g., may be convex or concave.

The control computer 18 controls controllable components, e.g., the laser source 22, the one or more optical mirrors 26 and/or scanner 24, in accordance with the control program 34. The control program 34 contains computer code that instructs the controllable components to focus the pulsed laser radiation at a region of the cornea to photodisrupt at least a portion of the region.

In certain examples of operation, the scanner 24 may direct the laser beam 36 to form or create a channel incision of any suitable geometry. One or more sections of the channel incision may be formed to extend two-dimensionally in an x-y plane (e.g., in a state when the cornea is flattened through abutment against the abutment face 38 of the contact element 30). In this respect, the scanner 24 may form one or more sections of the channel incision by focusing the laser beam 36 at a constant z-value under the abutment face 38 and moving the focus in a pattern in an x-y plane. Further, one or more sections of the channel incision may extend from under the anterior corneal surface in the direction of the surface of the cornea or to the surface of the cornea. The scanner 24 may form such one or more sections by changing the z-value of the focus of the laser beam 36 and optionally changing the x and/or y values.

Any suitable portion of the cornea may be photodisrupted. One or more of any of the corneal layers may be selected for photodisruption. In addition, a portion of a cell layer may be photodisrupted in the z-direction, but part of the cell layer may remain on the cornea. Moreover, a particular area (or "target zone") in an x-y plane may be selected for photodisruption.

The apparatus 10 may photodisrupt a corneal layer in any suitable manner. In certain embodiments, the control computer 18 may instruct the laser device 14 to focus the laser beam 36 at a constant z-value under the abutment face 38 and move in a pattern in an x-y plane that substantially covers the target zone. Any suitable pattern may be used.

As the laser beam 36 travels along the scan path, the laser radiation pulses create microdisruptions in the corneal tissue of the eye 12. In certain situations, a scan path pattern may yield a non-uniform distribution of microdisruptions over the target zone. In these cases, the laser beam 36 may be modified to make the distribution more uniform. For example, certain pulses may be blocked or the pulse energy may be decreased to reduce the number of or the effect of the pulses in a particular region.

The above procedure is similar to LASIK. In a way similar to LASIK, the control computer 18 may control the laser radiation source 22, one or more optical mirrors 26 and/or the scanner device 24. The control computer 18 may be programmed with the program 34 stored in the memory 20 to control the laser beam 36 in a special way to create the channel incision in the cornea of the eye 12. In contrast to LASIK, in the example shown in FIG. 1, the photodisruptions created by the laser radiation form a channel incision for the introduction of a photosensitizer rather than a flap.

After creation of the channel incision, a photosensitizer can be introduced into the eye 12 to change the biomechanical and/or biochemical properties of the eye 12 in a process known as "corneal crosslinking". For example, the mechanical stability of the cornea can be strengthened by the crosslinking. The eye 12 to be treated by crosslinking in this example is, without limitation, essentially the cornea, which is covered externally by a tear film. The cornea has an epithelium, a Bowman layer, a stroma, a Decement membrane and an endothelium.

After the introduction of the photosensitizer into the created channel incision, the photosensitizer can penetrate into and through the channel incision and from there distribute itself in the corneal tissue by diffusion.

In the process of the corneal crosslinking, after the introduction of the photosensitizer, the photosensitizer is to be exposed to UV light in order to be activated for corneal crosslinking. For this purpose, the photosensitizer is to be irradiated with light provided by the same laser source 22, which also provided the laser radiation for creating the channel incision. However, using the laser radiation without any modifications would result in photodisruptions to be created by the laser radiation in the cornea rather than just activation of the photosensitizer for corneal crosslinking. In order to prevent the creation of photodisruptions in the cornea, it is contemplated to reduce the fluence of the laser radiation which actually impinges on the cornea of the eye 12. The fluence reduction can be achieved in various ways, some of which being described in the following by way of example.

In accordance with a first example, it is possible to relocate or reposition the patient to be treated in order to change the position of the eye 12 relative to the apparatus 10. For example, the eye 12 is positioned further away from the contact element 30 in the z-direction. By maintaining the settings of the apparatus 10, the laser beam 36 is defocused, i.e., the focus of the laser beam 36 does not lie within the cornea but in front of the cornea. In this way, the fluence of the laser beam 36 within the cornea is reduced. It is conceivable to reposition the patient such that the distance of the eye 12 from the contact element 30 causes the laser beam 36 to be defocused in such a way that the fluence of the laser beam 36 within the cornea is (just) below a photodisruption threshold. The photodisruption threshold may be 1 Joule/$cm^2$, for example, dependent on the number of pulses and the source of laser radiation used. The distance may be calculated by the program 34. The photodisruption threshold may be the energy density at which photodisruption occurs in the cornea. Instead of repositioning the patient, the patient adapter 16 may be removed or replaced by another patient adapter, thereby modifying, e.g., defocusing, the laser beam 36 to cause activation of the photosensitizer rather than photodisruptions in the cornea.

According to a second example, a fluence reduction component 40 for reducing the fluence of the laser radiation may be provided. The fluence reduction component is configured to reduce the fluence of the laser radiation such that the reduced fluence is below a threshold at which corneal photodisruption occurs. In this way, the photosensitizer can be activated by irradiating the photosensitizer with the laser radiation, as provided by the source 22 with unchanged settings, the laser radiation having the reduced fluence.

The fluence reduction component 40 can be selectively introduced into the beam path of the laser beam 36. For example, the fluence reduction component 40 may be introduced into the beam path of the laser beam 36 in accordance with an instruction of the control computer 18. The fluence reduction component 40 may be introduced into the beam path of the laser beam 36 by swinging, swiveling, linearly moving or otherwise moving the fluence reduction component 40 into the beam path of the laser beam 36 or by mounting the fluence reduction component 40 at or attaching the fluence reduction component 40 to a component of the apparatus 10 in the beam path of the laser beam 36.

According to a first possible realization, the fluence reduction component 40 comprises or is configured as a defocusing component for defocusing of the laser beam 36. For example, the location of the defocused focus may lie in front of the eye 12 rather than in the eye. This results in the fluence of the laser beam 36 within the cornea to be reduced. The defocusing component may be configured such that the fluence of the laser beam 36 may be reduced below the threshold at which corneal photodisruption occurs.

According to a second possible realization, the fluence reduction component 40 comprises or is configured as a widening component for widening of the laser beam 36. The widening component may comprise a lens arrangement for widening of the laser beam 36. For example, the lens arrangement may comprise multiple, e.g., two or more lenses. By means of the widening component, the focus location of the laser beam 36 may be changed. For example, the location of the changed focus may lie in front of the eye 12 rather than in the eye 12. This results in the fluence of the laser beam 36 within the cornea to be reduced. The widening component may be configured such that the fluence of the laser beam 36 may be reduced below the threshold at which corneal photodisruption occurs.

Figure 2:
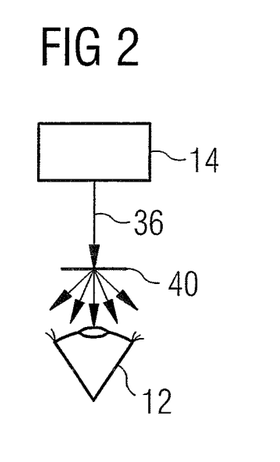
FIG. 2 schematically illustrates a variant of the apparatus for corneal crosslinking of FIG. 1.

According to a third possible realization, which is by way of example schematically illustrated in FIG. 2, the fluence reduction component 40 comprises or is configured as a scattering component for scattering of the laser beam 36. For example, the scattering component may comprise or be configured as a light scattering foil or as a disc diffuser such as a surface diffuser or a volume diffuser. The surface diffuser may comprise or consist of ground glass and may additionally be coated with anti-reflect coatings. The volume diffuser may comprise or consist of opal glass. Independent of the exact configuration of the scattering component, the scattering component may be adapted to scatter the laser beam in order to reduce the energy density of the laser beam in the cornea. This results in the fluence of the laser beam 36 within the cornea to be reduced. The scattering component may be configured such that the fluence of the laser beam 36 may be reduced below the threshold at which corneal photodisruption occurs.

According to a fourth possible realization, the fluence reduction component 40 comprises or is configured as an energy reduction component for reducing the energy of the laser radiation as provided by the source. By means of the energy reduction component, the energy of the laser beam 36 provided by the laser source 22 can be reduced. In consequence, the fluence of the laser beam 36 may be reduced below the threshold at which corneal photodisruption occurs. For example, the control computer 18 may determine the amount of energy reduction and may instruct the laser source 22 to reduce the energy by the determined amount.

Figure 3:
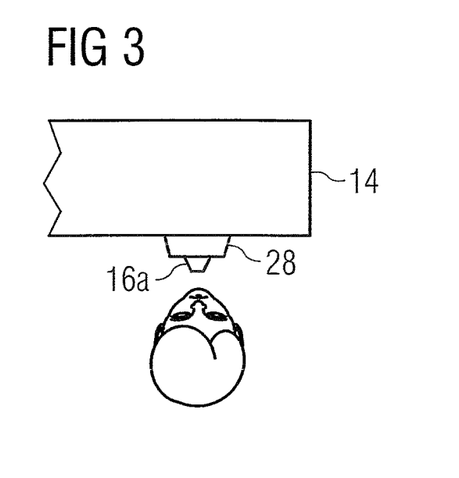
FIG. 3 schematically illustrates a variant of the apparatus for corneal crosslinking of FIG. 1.

In FIG. 1, it is shown by way of example, that the fluence reduction component 40 can be selectively moved into the beam path of the laser beam 36. Alternatively, as schematically illustrated in FIG. 3, the fluence reduction component may be part of the patient adapter 16 or another patient adapter 16a which can be exchanged with the patient adapter 16. As illustrated in FIG. 3, the patient adapter 16a is coupled with the laser device 14. The patient adapter 16a differs from the patient adapter 16 in that it comprises a fluence reduction component. Alternatively, the fluence reduction component 40 may be integrated into the laser device 14. In this case, the fluence reduction component 40 may be selectively introduced into the beam path of the laser beam 36.

Figure 4:
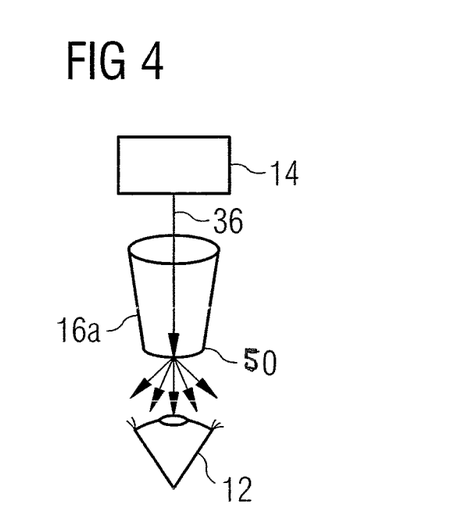
FIG. 4 schematically illustrates a variant of the apparatus for corneal crosslinking of FIG. 1.

Details of the patient adapter 16a are schematically shown in FIG. 4. The patient adapter 16a may exemplarily comprise a scattering component 50 for scattering the laser beam 36 as set forth above. Alternatively, any other suitable type of fluence reduction component may be contained in the patient adapter 16a.

Figure 5:
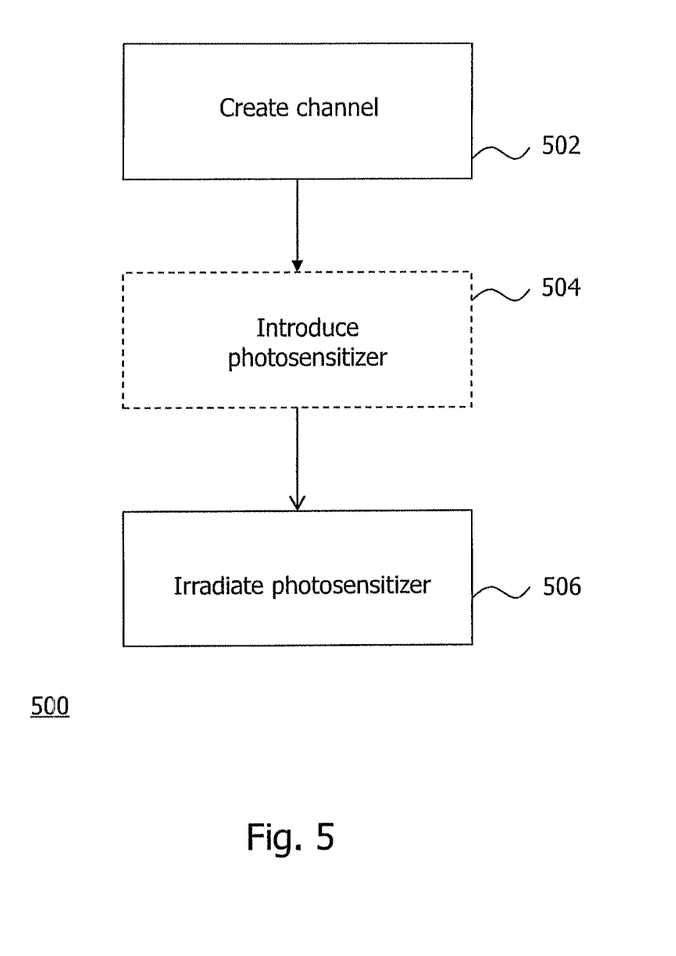
FIG. 5 illustrates an example of a method for corneal crosslinking in a human cornea according to an embodiment.

In FIG. 5, a method for corneal crosslinking according to an embodiment is schematically illustrated. In step 502, a scanner device (such as the scanner device 24 of FIG. 1) is controlled to create a channel incision in the cornea by means of a laser beam provided by a source of laser radiation (such as the source of laser radiation of FIG. 1). In step 504, a photosensitizer may be introduced into the created channel incision. Finally, in step 506, a scanner device (such as the scanner device 24 of FIG. 1) is controlled to activate the photosensitizer for corneal crosslinking by means of the laser beam. For performing step 506, the laser beam may have a reduced fluence. The fluence may have been reduced by any suitable fluence reduction component described above.

The invention claimed is:

1. An apparatus for corneal crosslinking, the apparatus comprising:
   a source of laser radiation having an energy and a pulse rate sufficient for creating photodisruption in a human cornea;
   a scanner device configured to scan the laser radiation;
   a control computer configured to control the scanner device;
   a fluence reduction component selected to reduce the fluence of the laser radiation below a threshold at which corneal photodisruption occurs and at a level sufficient to activate a photosensitizer, wherein the fluence reduction component is, in response to an instruction from the control computer, configured to be alternatively moved to a first position out of a beam path of the laser radiation and moved to a second position into the beam path of the laser radiation, the fluence reduction component comprising a lens arrangement; and
   the control computer further programmed to:

allow for the laser radiation having the energy and the pulse rate sufficient for creating photodisruption by moving the fluence reduction component to a first position out of the beam path of the laser radiation;

control the scanner device to create in the cornea, with the laser radiation, at least one incision for the introduction of or application of the photosensitizer into or onto the cornea; and reduce the fluence of the laser radiation to the level sufficient to activate the photosensitizer for corneal crosslinking by moving the fluence reduction component to a second position into the beam path of the laser radiation.

2. The apparatus of claim 1, wherein the reduced fluence is below a threshold at which corneal photodisruption occurs.

3. The apparatus according to claim 1, wherein the source for laser radiation is an ultraviolet femtosecond laser.

4. The apparatus according to claim 1, wherein the fluence reduction component comprises a defocusing component that defocuses the laser radiation.

5. The apparatus according to claim 1, wherein the fluence reduction component comprises a widening component comprising a lens arrangement that widens the laser radiation.

6. The apparatus according to claim 1, wherein the fluence reduction component comprises a light scattering foil.

7. The apparatus according to claim 1, wherein the fluence reduction component comprises a ground glass surface diffuser coated with an anti-reflect coating.

8. The apparatus according to claim 1, wherein the fluence reduction component comprises opal glass volume diffuser.

* * * * *